United States Patent
Menges et al.

(10) Patent No.: US 9,029,101 B2
(45) Date of Patent: May 12, 2015

(54) MICROPLATE READER WITH LID LIFTER FOR MICROPLATES

(71) Applicant: Tecan Trading AG, Mannedorf (CH)

(72) Inventors: Friedrich Menges, Berchtesgaden (DE); Harald Gebetsroither, Grodig (AT); Gyoergy Wenczel, Seekirchen (AT)

(73) Assignee: Tecan Trading AG, Mannedorf (CH)

( * ) Notice: Subject to any disclaimer, the term of this patent is extended or adjusted under 35 U.S.C. 154(b) by 0 days.

(21) Appl. No.: 13/956,551

(22) Filed: Aug. 1, 2013

(65) Prior Publication Data

US 2014/0045210 A1    Feb. 13, 2014

(30) Foreign Application Priority Data

Aug. 9, 2012    (CH) ........................................ 1306/12

(51) Int. Cl.
| | | |
|---|---|---|
| *C12M 1/34* | (2006.01) | |
| *G01N 21/01* | (2006.01) | |
| *G01N 21/64* | (2006.01) | |
| *G01N 35/02* | (2006.01) | |
| *G01N 35/04* | (2006.01) | |
| G01N 35/00 | (2006.01) | |

(52) U.S. Cl.
CPC .......... *G01N 21/6428* (2013.01); *G01N 35/028* (2013.01); *G01N 35/04* (2013.01); *G01N 2035/00287* (2013.01); *G01N 2035/0405* (2013.01); *Y10S 436/807* (2013.01)

(58) Field of Classification Search
CPC ................. B01L 1/00; B01L 2300/00; B01L 2300/0809; B01L 2300/0829; B01L 2400/0403; B01L 2400/043; G01N 1/00; G01N 2021/00; G01N 2021/0106; G01N 2021/15; G01N 2021/151; G01N 2035/00; G01N 2035/00178; G01N 2035/00277; G01N 2035/00287
See application file for complete search history.

(56) References Cited

U.S. PATENT DOCUMENTS

| | | | |
|---|---|---|---|
| 6,449,827 B1 | 9/2002 | Clarke et al. | |
| 7,666,362 B2 | 2/2010 | Shanler | |
| 2002/0041828 A1* | 4/2002 | Spitz et al. ...................... | 422/64 |
| 2011/0220239 A1* | 9/2011 | Reed et al. ........................ | 141/1 |
| 2011/0293488 A1 | 12/2011 | Nichols et al. | |

FOREIGN PATENT DOCUMENTS

| | | |
|---|---|---|
| DE | 201 01 734 | 7/2002 |
| EP | 0 114 259 | 8/1984 |
| EP | 1 192 995 | 4/2002 |
| EP | 1 640 723 | 3/2006 |
| WO | WO 93/08914 | 5/1993 |

OTHER PUBLICATIONS

Calderone, E.M. et al. 2001. Protocol and guide for estimating nucleic acids in larval fish using a fluorescence microplate reader. Northeast Fisheries Science Center. Reference Document 01-11, pp. 1-22; specif. pp. 5 and 10.*

* cited by examiner

*Primary Examiner* — John S Brusca
*Assistant Examiner* — Sharon M Papciak
(74) *Attorney, Agent, or Firm* — Notaro, Michalos & Zaccaria P.C.

(57) ABSTRACT

Microplate reader with optical measuring/detection device has housing, a microplate support and a moving unit. The moving unit moves the microplate support out and into the housing and horizontally within the housing. The reader has an integrated lid holding apparatus within the housing for lifting and placing a microplate lid on the microplate. The lid holding apparatus moves the microplate lid and/or the microplate support for moving the microplate in one respective vertical direction. A method for optically measuring a microplate in such a microplate reader places a covered microplate on the microplate support, retracts it into the housing, lifts the lid from the microplate, measures the microplate with the lifted lid, replaces the lid, and extends the support and the covered microplate out of the housing.

13 Claims, 4 Drawing Sheets

MICROPLATE READER WITH LID LIFTER FOR MICROPLATES

RELATED PATENT APPLICATIONS

This patent application claims priority of the Swiss patent application No. CH 01306/12 filed on Aug. 9, 2012, the entire content of which is incorporated herein by explicit reference.

RELATED FIELD OF TECHNOLOGY

The invention relates to a lid lifter for microplates which is installed in a microplate reader with at least one optical measuring/detection device. Microplates allow for example performing biological or biochemical tests in which a large number of samples are processed in parallel. Microplate readers have proven their worth in the optical evaluation of test results that are achieved in microplates.

All multi-well plates are designated as microplates in connection with the present invention which comprise a plurality of wells or containers which are arranged in an array. Especially preferred microplates at least approximately have the dimensions and footprint of a microplate according to the SBS standard, as published by the American National Standards Institute (ANSI). Microplates are known for example whose wells are provided with a round base, flat base or V bottom. The wells can be arranged as normal wells or deep wells. Wells in the form of a truncated cone or a truncated pyramid are known as well. It is a common feature in all microplates with different kinds of well shapes that they have a standardized base area, i.e. a standardized footprint, and that the axial distance of the wells respectively arranged in an array is also standardized. This axial distance is 18 mm in 24 well (4×6) plates, 9 mm in 96 well (8×12) plates, 4.5 mm in 384 well (16×24) plates, and 2.25 mm in 1536 well (32×48) plates. The height of a microplate can vary strongly depending on the type thereof and is typically between 10.4 mm (e.g. 1536 V base deep well plate) and 44 mm (e.g. 96 well Masterblock® of Greiner).

If biological or biochemical tests are performed in microplates over a prolonged period of time (over hours or even days) and/or at temperatures increased over room temperature, evaporation occurs often and typically, which can lead to a decrease in volume and changes in concentration of electrolytes and macromolecules up to drying up of the samples. For this reason, the microplates are preferably processed in a separate incubator, wherein the temperature and the air humidity are controlled in such a way that no evaporation will occur. It is disadvantageous that the microplates need to be transferred back and forth manually between the incubator and the reader. This discussion relates to the operation as a standalone reader. If the reader is a part of a robotic system on the other hand (larger laboratory installations, especially automated laboratory systems, usually comprise a robot which is usually provided with pipette tips for the transport of fluids or with grippers for the transport of laboratory items such as microplates or sample tubes; Freedom EVO® Liquid Handling Workstation of the current applicant can be mentioned as an example for such a laboratory system), the robot of this system assumes the transfer between the reader and the multiple incubator. The microplates could be processed alternatively in the reader itself, with the advantage that measuring cycles can be performed in between and automatically. It however would be disadvantageous in a robotic system to block a reader with a single microplate for days.

The evaporation of sample fluid from microplates is combated as a standard in such a way that the microplate is covered by a lid or that the microplate or its wells are sealed with self-adhesive or laminated foils. Such covering or closing leads to a number of disadvantages such as:

the use of a robotized injector for adding agents to the wells (e.g. for triggering luminescence reactions in the samples) is not possible;

the covering reduces the gas supply from the ambient environment to the wells, thereby leading to a deficiency in oxygen and/or carbon dioxide in the wells, which depending on the type of the cell will slow down cell growth, extend processing time and reduce the maximum achievable cell concentrations;

the gas exchange between the samples in the wells and the ambient environment is reduced or prevented, so that hazardous gas concentrations may form in the air space of the wells above the samples (e.g. in cell cultures or cell-based tests);

fluid evaporated from the samples may condensate on the bottom side of the lid or the self-adhesive foil, so that the condensation formed thereby will lead to erroneous optical measurements (e.g. the absorbance);

the lid and the self-adhesive foil will prevent or at least obstruct the optical detection of fluorescence in the samples by means of the preferred top detection (i.e. from above);

the lid and the self-adhesive foil will prevent the optical detection of luminescence in the samples by means of top detection.

Such problems were prevented at least partly until now in that the lid or the self-adhesive foil was removed before the insertion of a microplate into the microplate reader and the lid or the self-adhesive foil were mounted again after the termination of the measurement or the optical evaluation of the plate in the reader. It is obvious that such manipulations on microplates charged with sensitive samples is laborious and may even be potentially extremely damaging to the samples. In particular, cross contaminations may occur when re-mounting previously used self-adhesive foils. This is especially the case when in the course of a test protocol covering several days the same microplate is to be examined several times and at different times in the microplate reader. Furthermore, accidents cannot be excluded on the way between the location of the removal of the lid or the self-adhesive foil and the location of the microplate reader.

RELATED PRIOR ART

Solutions for the robotized removal of microplate lids are known from the state of the art:

The document US 2011/0293488 A1 for example discloses a specialized lid manipulation apparatus for the automatic lifting of a lid from a microplate or the placement of a lid thereon. The apparatus comprises a horizontally displaceable microplate support which can be moved out of the apparatus and can be equipped with a covered microplate. After the return of the microplate into the apparatus, a horizontally and vertically displaceable lid pressing apparatus will be placed above the microplate and lowered. After unlocking the special lid of the microplate, the lid will be lifted with a suction cup or alternatively with a robotic gripper. The microplate uncovered in this manner will subsequently be moved out of the apparatus together with the microplate support. The task of removing or placing the lid is performed in a relatively complex way. Furthermore, the use of this specialized lid manipulation apparatus requires a change or adjustment of the microplates to be used and the use of special lids.

The document U.S. Pat. No. 7,666,362 B2 describes the production and the use of a special microplate/lid combination, which can be handled by means of a robotic gripper. Although the advantage of the uncovering of the multiwell plate with the lid is recognized (reduction in the sample evaporation) and the person skilled in the art is obviously aware of robotic removal, the user must use these special microplates and lids and cannot use standard microplates and standard microplate lids.

The document EP 1 192 995 A2 discloses a special lid for standard microplates comprising a seal and a robotic gripper for holding the microplate and for the repeated removal and replacement of this special lid. The lid exerts a spring pressure on the seal, so that it is sealingly connected to the microplate. The robotic gripper is arranged to release the resilient parts of the lid according to this special lid construction and is arranged in a relatively complicated way. Although the user can use standard microplates, standard microplate lids cannot be used.

The document U.S. Pat. No. 6,449,827 B1 discloses a suction mechanism for tightly holding a microplate during the time of the removal of a microplate lid by means of a robotized gripper mechanism.

Even though the possibility is partly disclosed to use standard microplates and optionally even standard microplate lids, all known documents of the state of the art do not offer any solution to the problem of the frequently sensitive path of the microplate (and especially the uncovered samples) for the time between the lifting of the lid and the optical analysis of the samples in the microplate reader.

OBJECT AND SUMMARY OF THE PRESENT INVENTION

It is therefore the object of the present invention to propose an alternative apparatus and an alternative method which eliminates the disadvantages known from the state of the art.

This object is achieved according to a first aspect with a microplate reader according to the features as herein disclosed. This microplate reader comprises at least one optical measuring/detection device, a housing, a microplate support and a moving unit. The moving unit is arranged to move the microplate support out of the housing, into the housing and in at least one substantially horizontal direction within the housing. The microplate reader in accordance with the invention is characterized in that it comprises an integrated lid holding apparatus arranged within the housing for lifting a microplate lid from a microplate positioned on the microplate support and for placing a microplate lid onto a microplate, wherein said lid holding apparatus is arranged to move the microplate lid and/or the microplate support in one respective, at least approximately vertical direction for moving the microplate.

This object is achieved according to a second aspect by a method for optically measuring samples in wells of a microplate provided with a microplate lid in such a microplate reader as herein disclosed. The measuring method in accordance with the invention comprises the following steps:

(a) Placing a microplate covered by a microplate lid on the microplate support of the microplate reader;
(b) retraction of the microplate support and the covered microplate with the moving unit into the housing of the microplate reader;
(c) lifting of the microplate lid from the microplate positioned on the microplate support with a lid holding apparatus integrated in the microplate reader and arranged within the housing;
(d) measuring of the microplate with the lifted microplates lid by the at least one optical measuring/detection device;
(e) replacement of the microplate lid on the microplate positioned on the microplate support by using the lid holding apparatus integrated in the microplate reader, and
(f) extension of the microplate support and the covered microplate out of the housing of the microplate reader by the moving unit.

Further preferred and inventive features are provided in the respective dependent claims.

Advantages of the microplate reader or measuring method in accordance with the invention comprise the following:

All known measuring methods (e.g. absorbance, fluorescence, luminescence) can be applied to lid-free or covered microplates, while the microplate can be covered by a lid outside of the measuring periods;
standard microplates and (optionally slightly modified) standard microplate lids can be used;
in the case of cell-based tests the protection from evaporation by covering can be combined with the provision of sufficient gas exchange by brief exposure of the microplates;
automated injecting of agents (e.g. triggering luminescence or other reactions) is possible while performing tests in lid-protected microplates.

BRIEF INTRODUCTION OF THE ATTACHED DRAWINGS

An exemplary microplate reader in accordance with the invention will be shown by reference to schematic diagrams. These diagrams shall document selected embodiments of the microplate reader in accordance with the invention, which do not limit the scope of the present invention. It is shown in:

FIG. 1 a vertical sectional view through a microplate reader with extended moving unit and microplate support, after the manual or robotized positioning of a covered microplate on the microplate support;

FIG. 2 a vertical sectional view through a microplate reader with retracted moving unit and microplate support, prior to the lifting of the microplates lid with an integrated lid holding apparatus;

FIG. 3 a vertical sectional view through a microplate reader with retracted moving unit and microplate support, during lifting of the microplate lid with a magnetic lifter of the integrated lift holding apparatus;

FIG. 4 a vertical sectional view through a microplate reader with retracted moving unit and microplate support, wherein the microplate with lifted microplate lid is ready for measurement;

FIG. 5 a vertical sectional view through a microplate reader with retracted moving unit and microplate support during optical measurement of the microplate with lifted microplate lid and with corrected working distance to the measuring/detection device;

FIG. 6 a vertical sectional view through a microplate reader with retracted moving unit and microplate support during placement of the microplate lid on the microplate;

FIG. 7 a vertical sectional view through a microplate reader with retracted moving unit and microplate support during the movement away of the re-covered microplate by the magnetic lifter of the integrated lid holding apparatus;

FIG. 8 a vertical sectional view through a microplate reader with extended moving unit and microplate support during manual or robotized removal of the re-covered microplate from the microplate support;

FIG. 9 shows top views of standard microplate lids modified with self-adhesive iron foil, wherein

DETAILED DESCRIPTION OF THE PRESENT INVENTION

Figure 1:
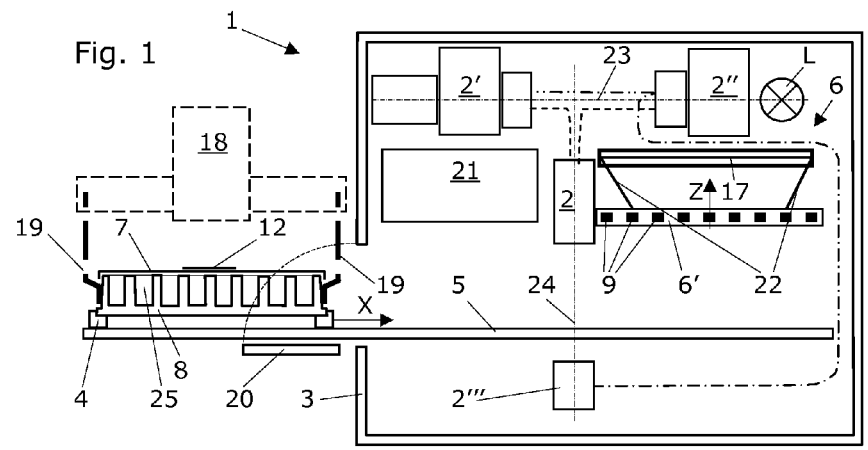

FIG. 1 shows a vertical sectional view through a microplate reader 1 with extended moving unit 5 and microplate support 4, after the manual or robotized positioning of a covered microplate 8 on the microplate support 4. The microplate reader 1 comprises a control unit 21 for monitoring and checking the functions of the reader and the moving unit 5.

The microplate reader 1 as shown here comprises at least one optical measuring/detection device 2. The microplate reader 1 further comprises a housing 3, a microplate support 4 and a moving unit 5, wherein the moving unit 5 is arranged to move the microplate support 4 out of the housing 3, into the housing 3 and, within the housing 3, in at least one substantially horizontal direction. The housing 3 is preferably optically sealed against the ambient environment. The housing can also be insulated with respect to the temperature, the gas composition and its relative humidity against the ambient environment and can therefore be arranged as a climatic chamber.

This optical measuring/detection device 2 can also be referred to as a "measuring head" and can be fixed in a stationary manner, i.e. in an immobile way. In this case, the moving unit 5 is additionally arranged in a height-movable way for focusing the optical measuring/detection device 2. Alternatively, the optical measuring/detection device 2 can be arranged in a height-displaceable manner, so that it can be moved from a parking position to a measuring position for example, wherein such a measuring head 2 preferably comprises at least one fine Z drive which is arranged to focus the optical measuring/detection device 2. A further alternative comprises the arrangement of a height-movable optical measuring/detection device 2 and a height-movable moving unit 5. For the purpose of focusing the optical measuring/detection device 2, the measuring head 2 will preferably be equipped in this case with a fine Z drive for focusing the optical measuring/detection device.

The microplate reader 1 further comprises an integrated lid holding apparatus 6 arranged within the housing 3 for lifting a microplate lid 7 from a microplate 8 positioned on the microplate support 4 and for placing a microplate lid 7 on a microplate 8. Preferably, the lid holding apparatus 6 is arranged to lift a microplate lid 7 from a microplate positioned on the microplate support 4 for holding said microplate lid 7 during the optical measurement of the microplate 8 and for placing said microplate lid 7 on the same microplate 8. It can alternatively be provided that the lid holding apparatus 6 is arranged in such a way that the microplate lid 7 can be placed within the housing 3 of the microplate reader 1 during the measurement of the microplate 8.

For the purpose of moving the microplate lid 7 away from the microplate 8, the lid holding apparatus 6 and/or the microplate support 4 can be arranged in one respective, approximately vertical direction. As a result, either the microplate lid 7 is lifted from the microplate 8, or the microplate 8 is lowered in relation to the microplate lid 7. A third possibility is the moving of the microplate lid 7 and the microplates 8 away from each other.

The exemplary microplate reader 1 as shown in FIGS. 1 to 8 comprises a lid holding apparatus 6 which is arranged as a magnetic lifter 6'. Said lid holding apparatus 6 comprises an array of permanent magnets 9. Said lid holding apparatus 6 is fixed here by means of flexible or pliable elements 22 to a carrying apparatus 17. Said flexible or pliable elements 22 are preferably attached in such a way (as illustrated) that their fixing locations on the carrying apparatus 7 are situated further apart than their fastening members on the magnetic lifter 6'. This arrangement automatically leads to an effective self-centering of the magnetic lifter 6' and additionally efficiently dampens its natural oscillations. The carrying apparatus 17 must therefore be arranged in a respectively cantilevered manner. These flexible or pliable elements 22 are preferably arranged as cords or ropes comprising metal. The illustrated carrying apparatus 17 is arranged in a height-adjustable way, wherein any movements are respectively indicated with a directional arrow and a "Z".

Figure 10:
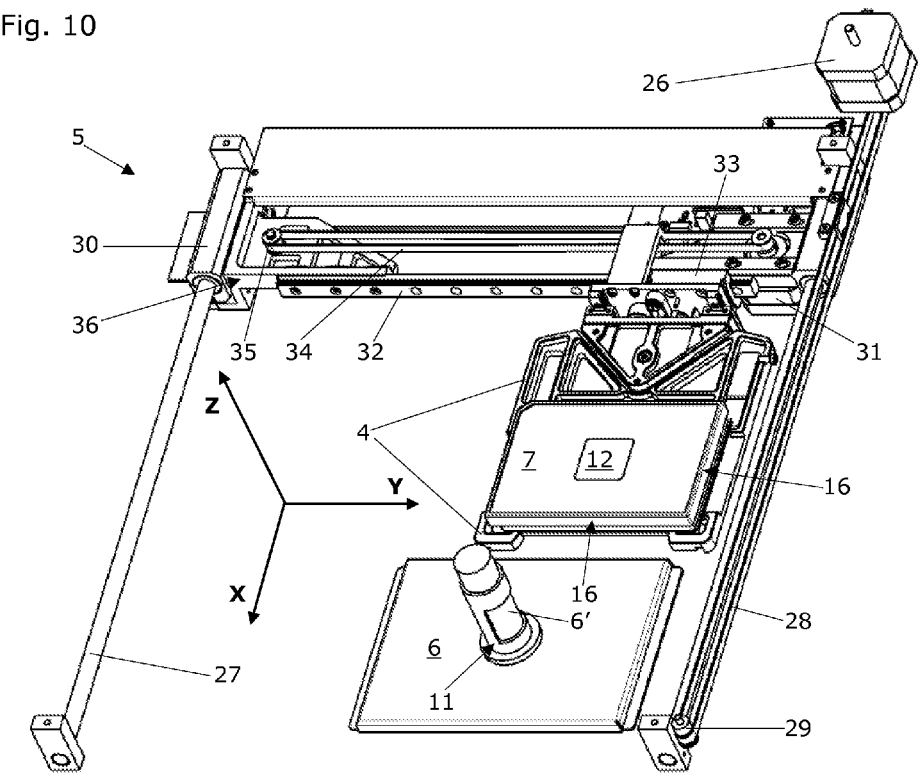
FIG. 10 shows a 3D view of the moving unit with a microplate with fitted microplate lid, which microplate is positioned on the microplate support.

Alternatively, the lid holding apparatus 6 can comprise an electromagnetic array 10 (not shown) or an individual switchable permanent magnet 11 (see FIG. 10). It is preferable in each of these cases that each microplate lid 7 to be lifted and placed comprises magnetizable material 12. The magnetizable material 12 is preferably chosen from a group which comprises self-adhesive metal foils, applied metallic lacquers, insert-molded metallic chips or metallic grains, and metal plates or metal foils that are insert-molded or back-molded with plastics. The metals are preferably chosen from the group which comprises iron, nickel, cobalt and their alloys, and alloys of these metals with non-magnetizable metals.

The exemplary microplate reader 1 shown in FIG. 1 further comprises an optical axis 23 which is arranged in a substantially horizontal way and a detection axis 24 which is arranged in a substantially vertical way. On the optical axis 23 and above the moving unit 5, arranged with the microplate support 4, said microplate reader 1 comprises detection optics 2', a light source L and first excitation optics 2". Furthermore, this microplate reader 1 comprises second excitation optics 2''', which is arranged beneath the moving unit 5 with the microplate support 4 and on the detection axis 24. The measuring head 2, i.e. the optical measuring/detection device, is also arranged on the detection axis 24, but above the moving unit 5 with the microplate support 4. The individual optical elements 2,2',2",2''' are preferably connected by means of fiber optics to each other, which is schematically indicated here by dot-dash and dashed lines (without necessarily representing the best or actual connection path).

A downwardly folding door 20 was opened for extending the moving unit 5 with the microplate support 4 from the housing 3 of the microplate reader 1. Instead of a downwardly folding door 20 it is also possible to provide a laterally displaceable door 20 for example (not shown). This alternative arrangement of the open door 20 facilitates receiving a microplate to be processed from a transfer station 37 positioned in front of the door 20 (see FIG. 11). This alternative arrangement of the open door 20 also supports the delivery of an already processed microplate to the transfer station 37 which is positioned in front of the door 20 (see FIG. 11). A further alternative arrangement of the open door is that the door 20 arranged as a flap will inwardly retract beneath the plate transport for opening. The placement of the microplate 8 on the microplate support 4 or the receiving of the magnet 8 from the microplate support 4 can occur (as illustrated) by a robot 18 equipped with gripper fingers 19 or also manually.

In a first alternative embodiment, the lid holding apparatus 6 can be arranged as a suction cup lifter 6″ (not shown) and comprises at least one suction cup 14 which can be connected to a vacuum source 13. Said vacuum source 13 is preferably arranged in the housing 3 of the microplate reader 1. It can also be arranged outside of the microplate reader 1 due to lack of available space for example. In a second alternative embodiment, the lid holding apparatus 6 can be arranged as a gripper 6′″ (not shown) and comprises at least two gripper fingers 15 for application to the lateral surfaces 16 of a microplate lid 7.

According to a preferred embodiment, the lid holding apparatus 6 is arranged to perform a lifting and lowering movement. According to an alternative embodiment, the lid holding apparatus 6 is arranged immovably in a stationary fashion. In this case however the moving unit 5 must be arranged to perform a lifting and lowering movement of the microplate support 4.

According to a similarly preferred embodiment, the optical measuring/detection device 2, i.e. the measuring head 2, is immovably arranged in a stationary fashion. It is also preferred to arrange the moving unit 5 to perform movements of the microplate support 4 in the X, Y, and Z directions of a Cartesian system of coordinates.

Figure 2:
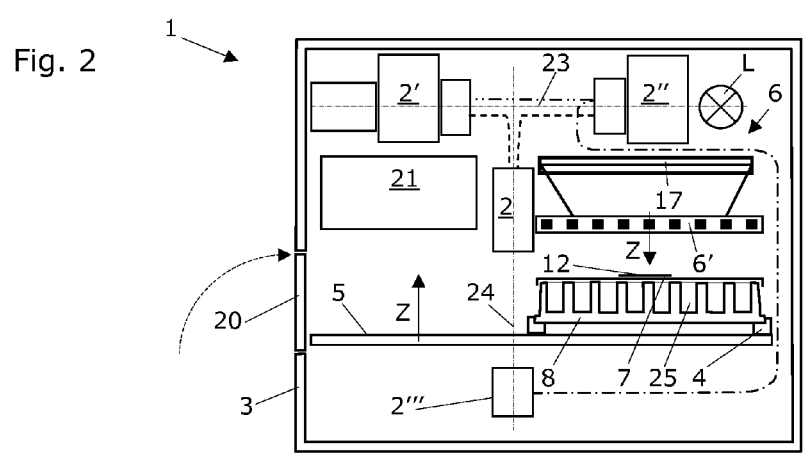
Figure 3:
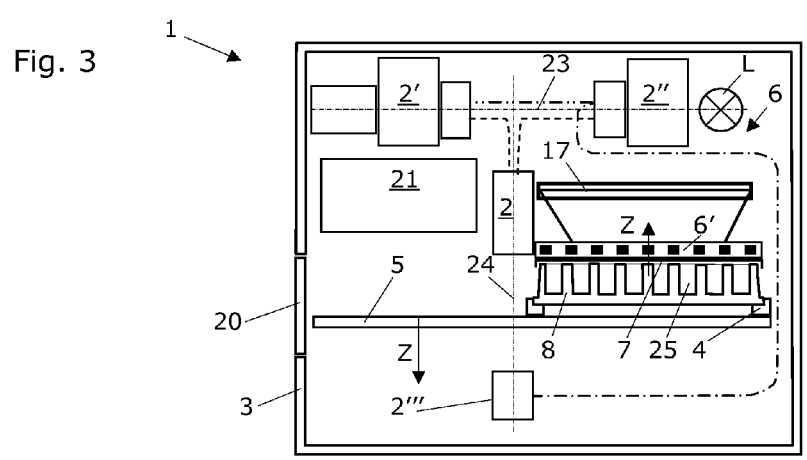
Figure 4:
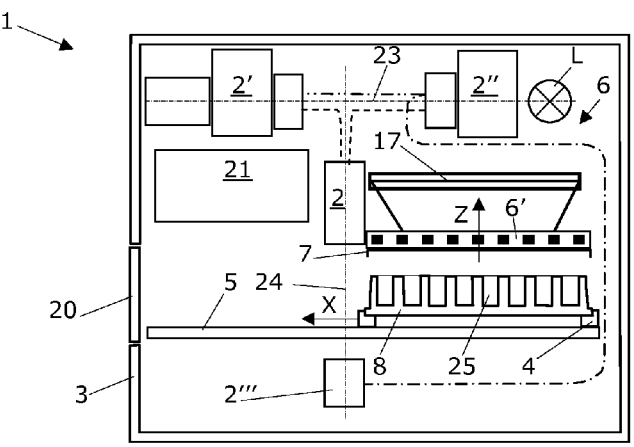
Figure 5:
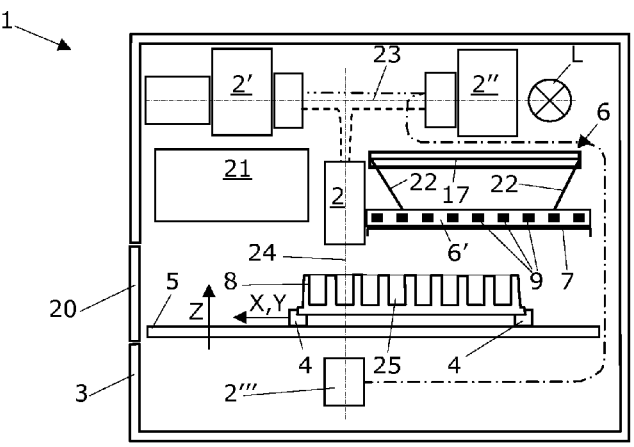
Figure 6:
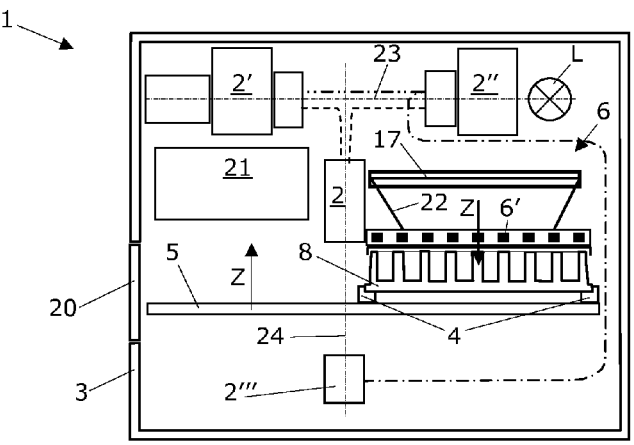
Figure 7:
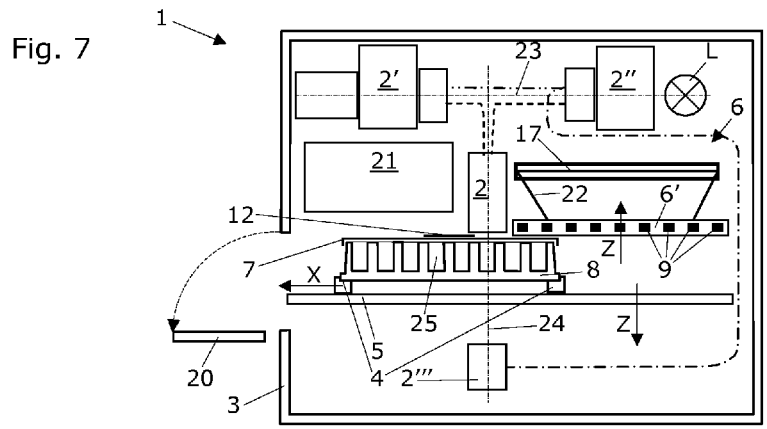
Figure 8:
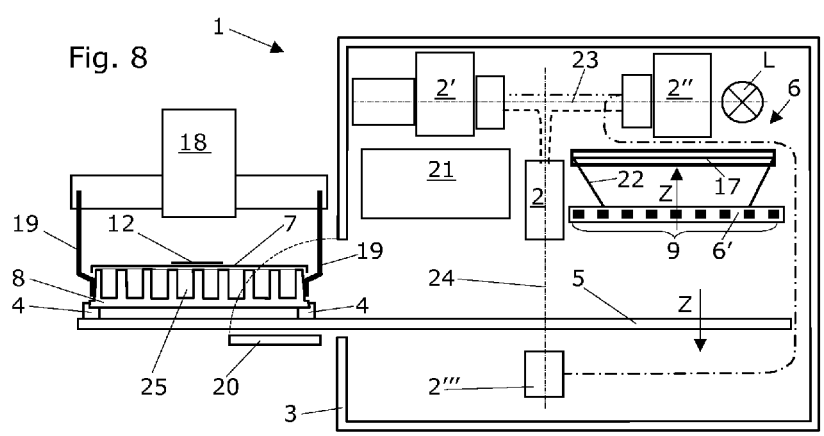

An exemplary method for optical measuring of samples in wells of a microplate 8 provided with a microplate lid 7 in a microplate reader 1 will now be explained in closer detail by reference to FIGS. 1 to 8. This method for measuring a microplate 8 will preferably be performed in a microplate reader 1 which comprises at least one optical measuring/detection device 2, a housing 3, a microplate support 4 and a moving unit 5. Preferably, the moving unit 5 is arranged to move the microplate support 4 out of the housing 3, into the housing 3 and, within the housing 3, in at least a substantially horizontal X direction. The method in accordance with the invention is characterized in that it comprises the following steps:

a) The placement of a microplate 8 covered by a microplate lid 7 on the microplate support 4 of the microplate reader 1. This is currently occurring in FIG. 1. The door 20 of the microplate reader 1 is preferably large enough that all possible microplate formats can be inserted by the moving unit 5 into the microplate reader 1.

b) The microplate support 4 and the covered microplate 8 are drawn by the moving unit 5 into the housing 3 of the microplate reader 1. This was just completed in FIG. 2 and the door 20 is closed. Preferably, all built-in parts of the microplate reader 1 are arranged to such an extent above the moving unit 5 and the microplate support 4 that all possible microplate formats can be moved by the moving unit 5 in the microplate reader 1.

c) The lifting of the microplate lid 7 from the microplate 8 positioned on the microplate support 4 by means of a lid holding apparatus 6 integrated in the microplate reader 1 and arranged within the housing 3 is prepared in FIG. 2 in that the microplate support 4 with the still covered microplate 8 is positioned in the receiving area of the lid holding apparatus 6. The lid holding apparatus 6 is subsequently lowered and/or the moving unit 5 is lifted with the microplate support 4 until the lid holding apparatus 6 comes into contact with the microplate lid 7, which is the case in FIG. 3. This establishment of contact is ensured in this case by means of a magnetizable material 12, which has been applied to the microplate lid 7 by way of example in form of a self-adhesive iron foil (see FIG. 1). Finally, the lid holding apparatus 6 is lifted and/or the moving unit 5 is lowered with the microplate support 4, so that the microplate 8 without the microplate lid 7 is ready for optical measurement of the samples in the wells 25 (see FIG. 4). As an alternative to the illustrated procedure with a lid holding apparatus 6 arranged as a magnetic lifter 6′, the microplate lid 7 can be lifted by a lid holding apparatus 6 which is arranged as a suction cup lifter 6″ or as a gripper 6′″.

d) The optical measurement of the microplate 8 with lifted microplate lid 7 by the at least one optical measuring/detection device 2 now occurs after the step-by-step displacement of the microplate 8 in the substantially horizontal X direction and Y direction, wherein each well 25 to be measured is moved into the detection axis 24 of the microplate reader 1. The optimal working distance between the microplate 8 and the measuring head 2 can be set by moving the microplate 8 and/or the measuring head 2 in a substantially vertical Z direction (see FIG. 5). The microplate lid 7 can be held during the measurement of the microplate 8 by the lid holding apparatus 6 within the housing 3 of the microplate reader 1 or be placed within the housing 3.

e) The replacement of the microplate lid 7 on the microplate 8 positioned on the microplate support 4 occurs by using the lid holding apparatus 6 integrated in the microplate reader 1 (see FIG. 6). For this purpose, the microplate 8 and the lid holding apparatus 6 are moved against each other in such a way that the microplate lid 7 is correctly placed on the microplate 8. In the case of the current use of a magnetic lifter 6′ with an array of permanent magnets 9 as a lid holding apparatus 6 and with a self-adhesive iron foil 12 on the microplate lid 7, the microplate lid 7 will be separated from the lid holding apparatus 6 in such a way that the microplate 8 with the microplate lid 7 placed thereon is horizontally displaced by the moving unit 5 (see FIG. 7). The microplate lid 7 will be stripped off from the bottom side of the lid holding apparatus 6 in this manner and will come to lie on the microplate 8.

f) The door 20 is opened again for the purpose of extending the microplate support 4 and the covered microplate 8 by the moving unit 5 from the housing 3 of the microplate reader 1 (see FIG. 8). The covered microplate 8 can be lifted from the extended microplate support 4 by means of a robot 18 equipped with gripper fingers 19 or by hand. The positioning of the microplate 8 on a transfer station 37 is also possible (see FIG. 11), from where it can be removed by means of the already described robot 18 or any other tool of any other laboratory implement that is suitable for this purpose.

A measuring method is also preferred in which the samples in the wells 25 of the microplate 8 are subjected to air and/or a reactant for triggering luminescence or other reactions between the lifting of the microplate lid 7 from the microplate 8 positioned on the microplate support 4 according to step c) and the optical measurement of the microplate 8 with lifted microplate lid 7 by the at least one optical measuring/detection device 2 according to step d).

The lifting and replacement of the microplate lid 7 in accordance with the invention in the interior of the microplate reader 1 (optionally in combination with a sample space arranged as a climatic chamber in the interior of the microplate reader 1) allows the performance of long-term tests and the monitoring of long-term kinetics (e.g. growth) of cell cultures in the wells 25 of microplate 8. The optical measurements on the samples to be performed sporadically and repeatedly are enabled by brief lifting and replacement of the microplate lid 7. Similarly, the addition of culture medium or other substances and agents to the cell cultures in the wells 25 of microplate 8 is enabled by brief lifting and replacement of the microplate lid 7. Such long-term tests are preferably performed in standalone microplate readers 1.

As is shown in FIGS. 1 to 8, it is preferable in the described measuring method that the microplate lid 7 is placed on the microplate 8 after the optical measurement of the microplate 8 by using the lid holding apparatus 6 within the housing 3 of the microplate reader 1, and the microplate support 4 and the covered microplate 8 are conveyed by the moving unit 5 out of the housing 3 of the microplate reader 1.

Figure 9A:
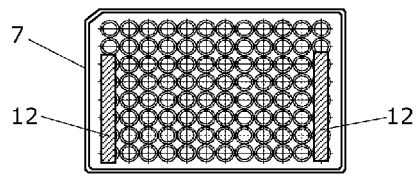
FIG. 9A shows two narrow, transversely disposed and extremely positioned strips on the lid for a 96 well microplate.
Figure 9B:
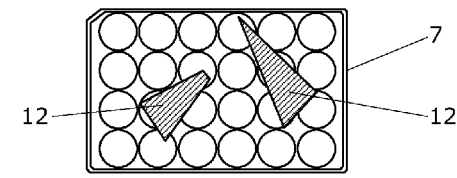
FIG. 9B shows two randomly positioned, at least approximately triangular pieces on the lid for a 24 well microplate.
Figure 9C:
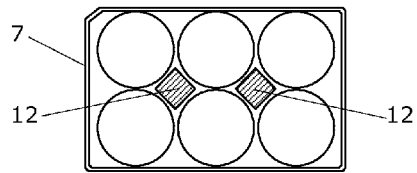
FIG. 9C shows two randomly positioned pieces on the lid for a 6 well microplate, which pieces are placed between the wells and are approximately square.
Figure 9D:
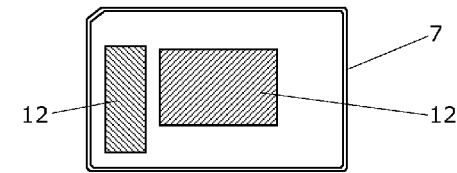
FIG. 9D shows two alternatives of at least approximately rectangular pieces on the lid for a random standard microplate.

FIG. 9 shows top views of standard microplate lids 7 modified by a self-adhesive iron foil 12. The magnetizable material 12 can almost be formed at will as a result of using an array of permanent magnets 9 and can nearly be arranged as required. The examples of the attachment of a self-adhesive iron foil 12 as shown in FIGS. 9A, 9B, 9C and 9D provide perfect lifting and replacement of the microplate lid 7 without exception, wherein:

- two narrow, transverse and extremely positioned strips 12 were glued onto the lid 7 for a 96 well microplate (see FIG. 9A);
- two randomly positioned, at least approximately triangular pieces 12 were glued onto the lid for a 24 well microplate (see FIG. 9B);
- two randomly positioned, at least approximately square pieces 12 were glued onto the lid 7 for a 6 well microplate (see FIG. 9C);
- two alternatives of at least approximately rectangular pieces 12 were glued onto the lid 7 for a random standard microplate (see FIG. 9D).

The use of such an array of permanent magnet 9 solves the problem of spontaneous displacement of the microplate lid 7 during lifting from the microplate 8. Such displacement can occur especially when the magnetic lifter 6' of the lid holding apparatus 6 is equipped with only one single permanent magnet or electromagnet, when this magnet has a substantially smaller area than the microplate lid 7 to be received, and when the magnetizable material 12 on or in the microplate lid 7 has a similar area as the magnet but is arranged in projection offset to the magnet. If in such a case the lid holding apparatus 6 with the magnetic lifter 6' approaches the microplate lid 7 to be lifted, this microplate lid 7 will be subjected to spontaneous horizontal displacement according to the horizontal displacement of the magnetizable material 12 in relation to the individual magnet of the magnetic lifter 6'. It is obvious that such a displaced microplate lid 7 can no longer be correctly replaced on the microplate 8 in an automated fashion. This displacement problem can be solved on the one hand in such a way that (as illustrated) an array of permanent magnets 9 is used instead of the individual magnet. On the other hand, this displacement problem can be solved in such a way that the individual magnet of the magnetic lifter 6' and the magnetizable material 12 are mounted precisely on top of one another in projection.

A further possibility to solve this displacement problem is that the lid holding apparatus 6 comprises a plate made of a magnetizable material (e.g. of iron, nickel cobalt, or a metallic alloy comprising at least one of these metals) instead of the magnetic lifter 6', wherein this plate preferably has a surface which is larger than the surface of the microplate lid 7 to be received (not shown). The fixing of a magnetic material (e.g. a magnetic foil or an individual permanent magnet) on the microplate lid (not shown) will then be sufficient for example. Similarly, the lid holding apparatus 6 may comprise a magnetizable material 12 which is selected from a group which comprises self-adhesive metal foils, applied metallic lacquers, insert-molded metallic chips or metallic grains, and metal plates or metal foils that are inserted-molded or back-molded with plastics.

FIG. 10 shows a 3D view of the moving unit 5 with a microplate 8, whereon the microplate lid 7 with side surfaces 16 and a magnetizable material 12 is placed, positioned on the microplate support 4. The Cartesian system of coordinates is indicated by the three arrows (X, Y and Z). The moving unit 5 comprises two parallel guide rods 27, on which one respective slide bearing 30 is arranged. These two slide bearings 30 are connected to each other via a carriage 36. A first motor 26 moves said carriage 36 in an X direction of a Cartesian system of coordinates with a first toothed belt guided over a first deflection pulley 29. The microplate support 4 is fixed to the said carriage 36 by means of a link 33, wherein said link 33 is movably guided along a linear guide 32 and along the carriage 36. A second motor 31 moves the link 33 with the microplate support 4 in a Y direction of the Cartesian system of coordinates by means of a second toothed belt 34 which is guided via a second deflection pulley 35. The moving device 5 as described above is preferably movable in a Z direction of the Cartesian system of coordinates (not shown in FIG. 10).

FIG. 10 further shows a lid holding apparatus 6 with a magnetic lifter 6', which comprises a single switchable permanent magnet 11. Switchable permanent magnets are known from the state of the art (cf. EP 0 114 259 B1 for example) and will be adjusted by a person skilled in the art with knowledge of the present invention in its construction and arrangement to the requirements for lifting a microplate lid 7.

Instead of the lid holding apparatus 6 with a magnetic lifter 6', a person skilled in the art, with knowledge of the present invention, can easily provide a lid holding apparatus 6 which is arranged as a suction cup lifter 6" or as a gripper 6''', wherein said person would coordinate any required lifting and lowering movement of the lid holding apparatus 6 with the movements of the moving unit 5 for performing movements of the microplate support 4 in the X, Y and Z directions of a Cartesian system of coordinates.

Figure 11:
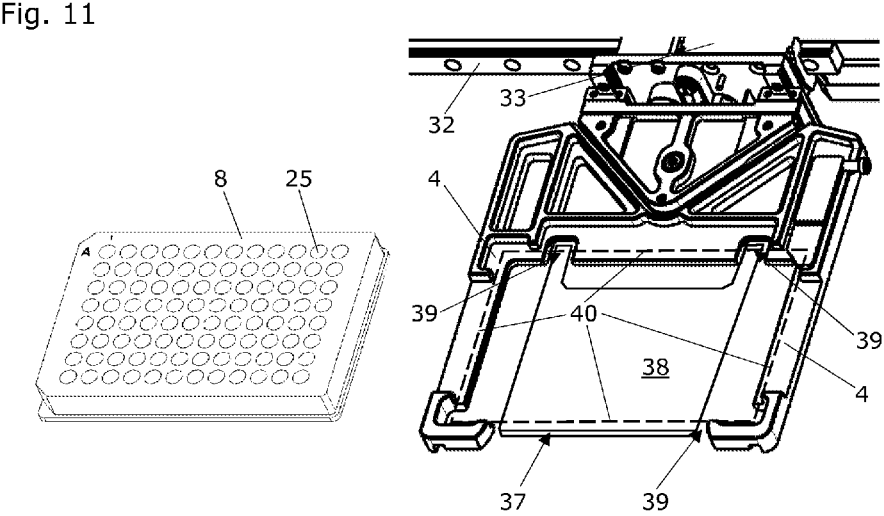
FIG. 11 shows a slightly enlarged 3D view of the empty microplate support of the moving unit at a transfer station and in the respective enlargement a 3D view of a 96 well microplate without microplate lid.

FIG. 11 shows a slightly enlarged 3D view of the empty microplate support 4 of the moving unit 5 (according to FIG. 10) at a transfer station 37 and in the respective enlargement a 3D view of a 96 well microplate 8 without the microplate lid 7. The transfer station 37 comprises a support plate 38 of a shape adjusted to the microplate support 4, wherein the microplate support 4 comprises cut-outs 39 which protrude beyond the footprint 40 of a standard microplate 8, so that parts of the support plate 38 which protrude into these cut-outs 39 are sufficient for carrying the microplate 8.

The microplate support 4 of the moving unit 5 is extended for receiving a microplate 4 at the transfer station 37 in a Z level which is situated beneath the level of the support plate 38 of the transfer station 37 and therefore also beneath the footprint 40 of the microplate 8 of said support plate 38. After assuming a correct transfer position, the microplate support 4 is lifted in the Z direction until the microplate 8 rests on the microplate support 4. At the same time, the large cut-out 39 in the support plate 38 (at the bottom in FIG. 11) enables the transfer station 37 to be approached at a lower level than the surface of the support plate if said support plate 38 is to be supported by a central pillar (not shown) on a working surface of a laboratory workstation (not shown).

For the purpose of delivering the microplate 4 at the transfer station 37, the microplate support 4 of the moving unit 5 will be extended in a Z level which is situated above the level of the support plate 38 of the transfer station 37. After assuming a correct transfer position, the microplate support 4 is lowered in the Z direction until the microplate 8 rests on the support plate 38 of the transfer station 37.

The same reference numerals in the drawings designate the same or at least similar features, even if they are not described in detail in each case.

| List of reference numerals | |
|---|---|
| 1 | Microplate reader |
| 2 | Optical measuring/detection device, measuring head |
| 2' | Detection optics |
| 2" | First excitation optics |
| 2'" | Second excitation optics |
| 3 | Housing |
| 4 | Microplate support |
| 5 | Moving unit |
| 6 | Lid holding apparatus |
| 6' | Magnetic lifter |
| 6" | Suction cup lifter |
| 6'" | Gripper |
| 7 | Microplate lid |
| 8 | Microplate |
| 9 | Array of permanent magnets |
| 10 | Electromagnetic array |
| 11 | Single switchable permanent magnet |
| 12 | Magnetizable material |
| 13 | Vacuum source |
| 14 | Suction cup |
| 15 | Gripper finger of 6'" |
| 16 | Side surfaces of 7 |
| 17 | Carrying apparatus |
| 18 | Robot |
| 19 | Gripper finger of 18 |
| 20 | Door |
| 21 | Control unit |
| 22 | Flexible, pliable elements |
| 23 | Optical axis |
| 24 | Detection axis |
| 25 | Well of 8 |
| 26 | First motor |
| 27 | Guide rod |
| 28 | First toothed belt |
| 29 | First deflection pulley |
| 30 | Slide bearing |
| 31 | Second motor |
| 32 | Linear guide |
| 33 | Link |
| 34 | Second toothed belt |
| 35 | Second deflection pulley |
| 36 | Carriage |
| 37 | Transfer station |
| 38 | Support plate of 37 |
| 39 | Cut-outs of 38 |
| 40 | Footprint of 4 |
| L | Light source |

The invention claimed is:

1. A microplate reader (1), comprising:
at least one optical measuring/detection device (2),
a housing (3),
a microplate support (4); and
a moving unit (5),
wherein the moving unit (5) is arranged to move the microplate support (4) out of the housing (3), into the housing (3) and in at least one substantially horizontal direction within the housing (3),
wherein the microplate reader (1) comprises an integrated lid holding apparatus (6) arranged within the housing (3) for lifting a microplate lid (7) from a microplate (8) positioned on the microplate support (4) and for placing a microplate lid (7) on a microplate (8), wherein said lid holding apparatus (6) is arranged to move the microplate lid (7) and/or the microplate support (4) for moving the microplate (8) in one respective, at least approximately vertical direction,
wherein the lid holding apparatus (6) is arranged as a magnetic lifter (6') and comprises an array of permanent magnets (9) or an individual switchable permanent magnet (11), and
wherein each microplate lid (7) to be lifted or placed comprises magnetizable material (12) or at least one permanent magnet (9).

2. The microplate reader (1) of claim 1, wherein the lid holding apparatus (6) is arranged to lift a microplate lid (7) from a microplate (8) positioned on the microplate support (4), for holding said microplate lid (7) during the optical measurement of the microplate (8) and for placing said microplate lid (7) on said microplate (8).

3. The microplate reader (1) of claim 1,
wherein the magnetizable material (12) is chosen from a group which comprises self-adhesive metal foils, applied metallic lacquers, insert-molded metallic chips or grains, and metal plates or metal foils that are insert-molded or back-molded with plastics, and
wherein the metals are chosen from the group which comprises iron, nickel, cobalt and their alloys, and alloys of these metals with non-magnetizable metals.

4. The microplate reader (1) of claim 1,
wherein the lid holding apparatus (6) is fixed with flexible or pliable elements (22) to a carrying apparatus (17).

5. The microplate reader (1) of claim 1,
wherein the lid holding apparatus (6) is arranged to perform a lifting and lowering movement.

6. The microplate reader (1) of claim 1,
wherein the lid holding apparatus (6) is immovably arranged in a stationary manner and the moving unit (5) is arranged to perform a lifting and lowering movement of the microplate support (4).

7. The microplate reader (1) of claim 1,
wherein the optical measuring/detection device (2) is immovably arranged in a stationary manner.

8. The microplate reader (1) of claim 1,
wherein the moving unit (5) is arranged to perform movements of the microplate support (4) in the X, Y and Z directions of a Cartesian system of coordinates.

9. A method for optically measuring samples in wells (25) of a microplate (8) provided with a microplate lid (7) in a microplate reader (1), which comprises at least one optical measuring/detection device (2), a housing (3), a micro-plate support (4) and a moving unit (5), wherein the moving unit (5) is arranged to move the microplate support (4) out of the housing, into the housing (3) and in at least one substantially horizontal direction within the housing (3),
wherein the measuring method comprises the following steps:
(a) placing the microplate (8) covered by the microplate lid (7) on the microplate support (4) of the microplate reader (1), the microplate lid (7) comprising magnetizable material (12) or at least one permanent magnet (9);
(b) retracting the microplate support (4) and the covered microplate (8) by the moving unit (5) into the housing (3) of the microplate reader (1);
(c) lifting the microplate lid (7) from the microplate (8) positioned on the microplate support (4) with a lid holding apparatus (6) integrated in the microplate reader (1)

and arranged within the housing (3), the lid holding apparatus (6) being arranged as a magnetic lifter (6') and comprises an array of permanent magnets (9) or an individual switchable permanent magnet (11);

(d) measuring the microplate (8) with the lifted microplate lid (7) by the at least one optical measuring/detection device (2);

(e) re-placing the microplate lid (7) on the microplate (8) positioned on the microplate support (4) by using one or both of the lid holding apparatus (6) integrated in the microplate reader (1) and the microplate support (4), and (f) extending the microplate support (4) and the covered microplate (8) by the moving unit (5) from the housing (3) of the microplate reader (1).

10. The measuring method of claim 9, wherein the microplate lid (7) is held by the lid holding apparatus (6) within the housing (3) of the microplate reader (1) or placed in the housing (3) during the optical measurement of samples in wells (25) of the microplate (8).

11. The measuring method of claim 9, wherein the samples in the wells (25) of the microplate (8) are brought into contact with air and/or a reagent for triggering luminescence or other reactions between the lifting of the microplate lid (7) from the microplate (8) positioned on the microplate support (4) according to step (c) and the optical measurement of samples in wells (25) of the microplate (8) with lifted microplate lid (7) by the at least one optical measuring/detection device (2) according to step (d).

12. The measuring method of claim 9, wherein the microplate lid (7) is placed on the microplate (8) within the housing (3) of the microplate reader (1) by using the lid holding apparatus (6) after the optical measurement of the samples in wells (25) of the microplate (8), and the microplate support (4) and the covered microplate (8) are conveyed by the moving unit (5) out of the housing (3) of the microplate reader (1).

13. The measuring method of claim 9, wherein the microplate lid (7), for the optical measurement of samples in wells (25) of the microplate (8), is lifted and replaced several times during a long-term test.

* * * * *